(12) United States Patent
Huh

(10) Patent No.: US 11,376,161 B2
(45) Date of Patent: Jul. 5, 2022

(54) WELDER PROTECTOR

(71) Applicant: OTOS WING. CO., LTD., Seoul (KR)

(72) Inventor: Sung Won Huh, Seoul (KR)

(73) Assignee: OTOS WING.CO., LTD., Seoul (KR)

( * ) Notice: Subject to any disclaimer, the term of this patent is extended or adjusted under 35 U.S.C. 154(b) by 147 days.

(21) Appl. No.: 16/294,691

(22) Filed: Mar. 6, 2019

(65) Prior Publication Data

US 2019/0274885 A1 Sep. 12, 2019

(30) Foreign Application Priority Data

Mar. 9, 2018 (KR) .......................... 10-2018-0028302

(51) Int. Cl.
*A61F 9/06* (2006.01)
*A42B 3/22* (2006.01)

(52) U.S. Cl.
CPC .............. *A61F 9/067* (2013.01); *A42B 3/225* (2013.01)

(58) Field of Classification Search
CPC .. A61F 9/06; A61F 9/067; A61F 9/029; A61F 9/02; A42B 3/225; A41D 13/1153; A41D 13/1184; F16P 1/06
USPC ............................. 2/8.2, 6.7, 15, 7, 10, 431
See application file for complete search history.

(56) References Cited

U.S. PATENT DOCUMENTS

| 3,484,156 A * | 12/1969 | Militello | A61F 9/06 351/44 |
| 4,100,619 A * | 7/1978 | Piech | A42B 3/226 2/10 |
| 5,107,543 A * | 4/1992 | Hansen | A41D 13/1146 2/426 |
| 6,035,451 A * | 3/2000 | Burns | A42B 3/225 2/424 |
| 7,131,148 B1 * | 11/2006 | Traumer | A42B 1/041 2/426 |
| 2003/0150048 A1 * | 8/2003 | Price | A61F 9/025 2/431 |
| 2009/0113607 A1 * | 5/2009 | Lian | A41D 13/1184 2/427 |
| 2012/0186005 A1 * | 7/2012 | Anderson | A61F 9/028 2/452 |
| 2014/0259252 A1 * | 9/2014 | Seo | A61F 9/022 2/8.2 |
| 2015/0033430 A1 * | 2/2015 | Hofer Kraner | A61F 9/06 2/8.2 |

(Continued)

FOREIGN PATENT DOCUMENTS

KR 10-2014-0111730 A 9/2014

OTHER PUBLICATIONS

Korean Office Action for KR10-2018-0028302 dated Feb. 1, 2019, 5 pages.

*Primary Examiner* — Nathan E Durham
*Assistant Examiner* — Abby M Spatz
(74) *Attorney, Agent, or Firm* — Kilpatrick Townsend & Stockton LLP

(57) ABSTRACT

A welder protector for protecting a worker includes a face shield including a first opening and a shield surface part surrounding the first opening, goggles detachably coupled to the face shield and including a window portion and a wearing portion, the window portion corresponding to the eyes of the worker, the wearing portion extending around a head of the worker, and a helmet detachably coupled to the face shield and including a second opening corresponding to the face shield.

19 Claims, 16 Drawing Sheets

(56) References Cited

U.S. PATENT DOCUMENTS

2018/0133060 A1* 5/2018 Patel .................. F21V 23/0464
2019/0298574 A1* 10/2019 Seo ........................ G02C 11/00

* cited by examiner

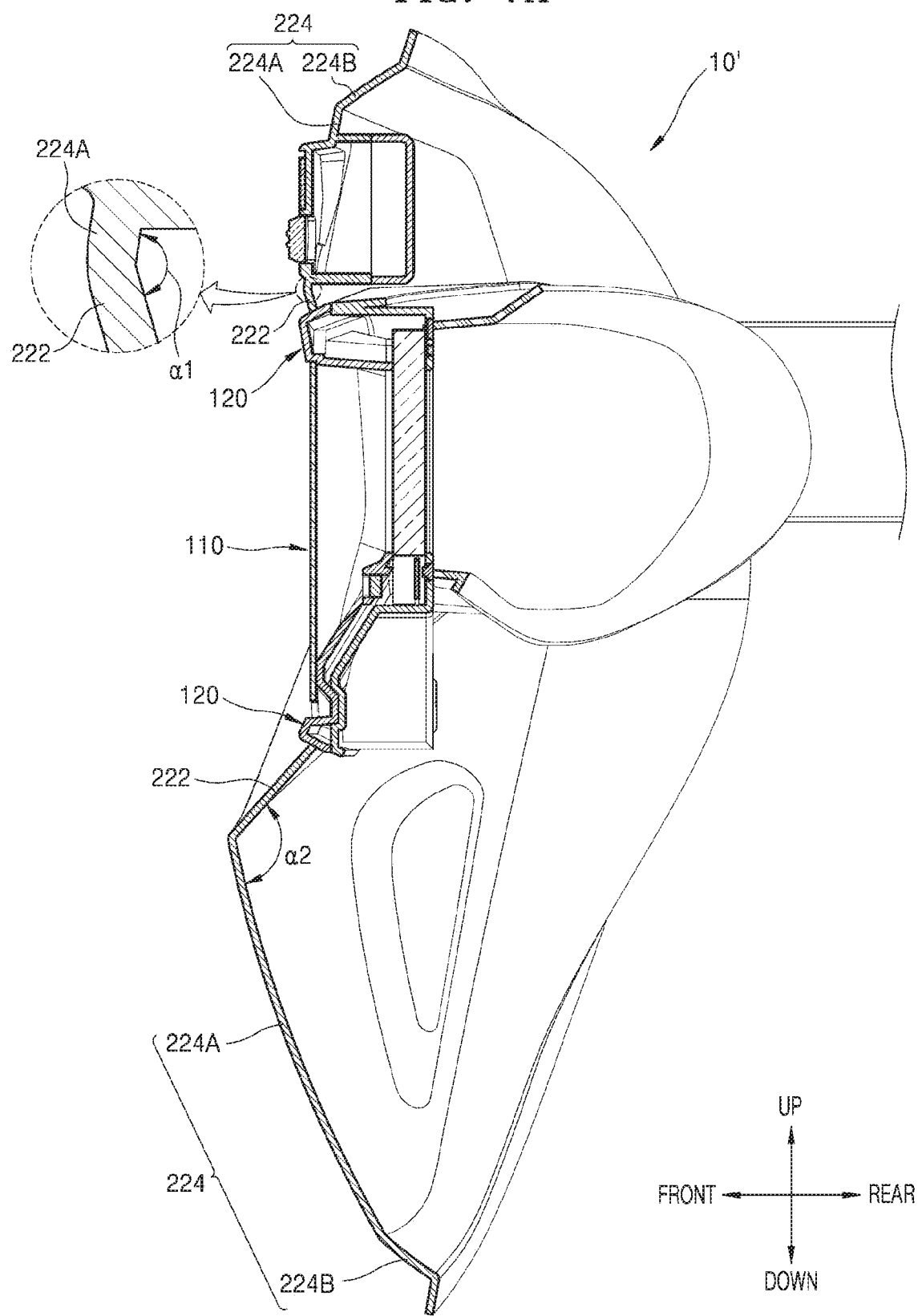

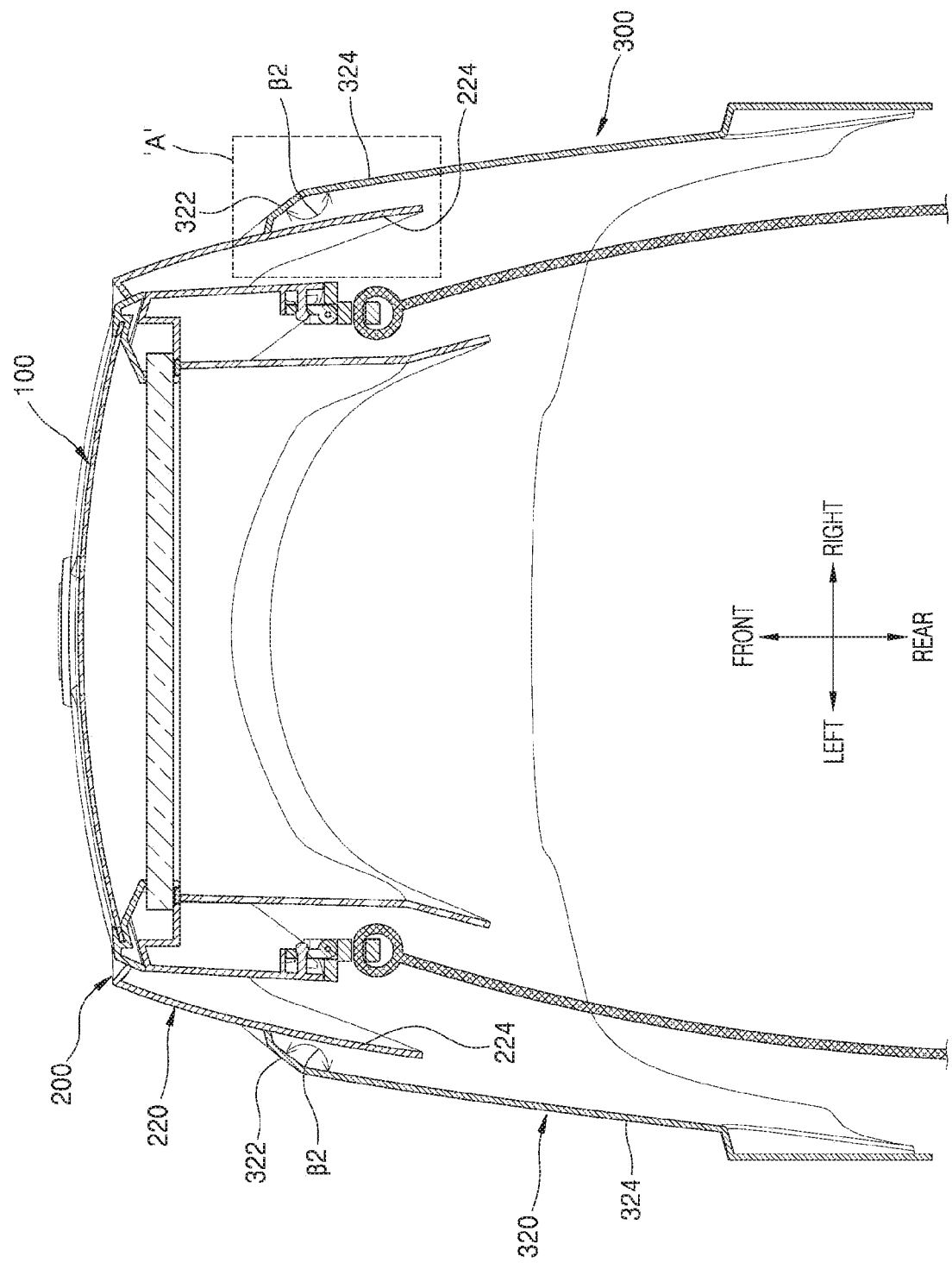

WELDER PROTECTOR

CROSS-REFERENCE TO RELATED APPLICATION

This application claims the benefit of Korean Patent Application No. 10-2018-0028302, filed on Mar. 9, 2018, in the Korean Intellectual Property Office, the disclosure of which is incorporated herein in its entirety by reference.

BACKGROUND

1. Field

One or more embodiments relate to a welder protector, and more particularly, to a structure of a welder protector having at least a part that is combinable or separable according to the worker's choice.

2. Description of the Related Art

Protective equipment has been worn to protect workers from light and high heat generated during a welding process such as arc welding. The protective equipment may have various shapes and structures such as a shape covering the worker's eyes or a shape covering the head of a user depending on the work content of the worker.

SUMMARY

During work such as welding, a worker may wear protective equipment having a particular shape among a variety of types of protective equipment considering work purposes and environments. It is inconvenient for a worker to wear different protective equipment according to the work content such as a welding portion and the intensity of a flame used for welding.

One or more embodiments include a welder protector which may have a shape easily deformable according to the work content and protect the body of a worker in various ways.

Additional aspects will be set forth in part in the description which follows and, in part, will be apparent from the description, or may be learned by practice of the presented embodiments.

According to one or more embodiments, a welder protector for protecting a worker includes a face shield including a first opening and a shield surface part surrounding the first opening, goggles detachably coupled to the face shield and including a window portion and a wearing portion, the window portion corresponding to the eyes of the worker, the wearing portion extending around a head of the worker, and a helmet detachably coupled to the face shield and including a second opening corresponding to the face shield.

When the goggles and the face shield are coupled to each other, a first surface part of the goggles provided around the window portion may contact an inner edge of the shield surface part, the inner edge defining the first opening.

The shield surface part of the face shield may include a main surface part covering a side portion of the goggles and a bent surface part bent toward the first opening from the main surface part to form an angle with the main surface part.

The welder protector may further include a protrusion, wherein, when the goggles and the face shield are coupled to each other, the protrusion is adjacent to an edge of the first opening and is arranged in an inner space between the goggles and the face shield.

The protrusion may protrude from the first surface part to at least partially cover a contact portion between the first surface part of the goggles and an inner edge of the face shield.

The face shield may further include an additional protrusion contacting the protrusion.

The goggles may include a transparent substrate and an electronic optical element that is disposed inside the transparent substrate and includes liquid crystal.

The helmet may include a protection surface part surrounding the second opening, and the face shield may be coupled to the helmet by proceeding from the inside of the helmet toward the second opening such that the shield surface part contacts an inner edge of the protection surface part.

BRIEF DESCRIPTION OF THE DRAWINGS

These and/or other aspects will become apparent and more readily appreciated from the following description of the embodiments, taken in conjunction with the accompanying drawings in which:

FIG. 7A is a cross-sectional view taken along line VIIa-VIIa of FIG. 6;

FIG. 10B is a cross-sectional view taken along line Xb-Xb of FIG. 1; and

DETAILED DESCRIPTION

Figure 1:
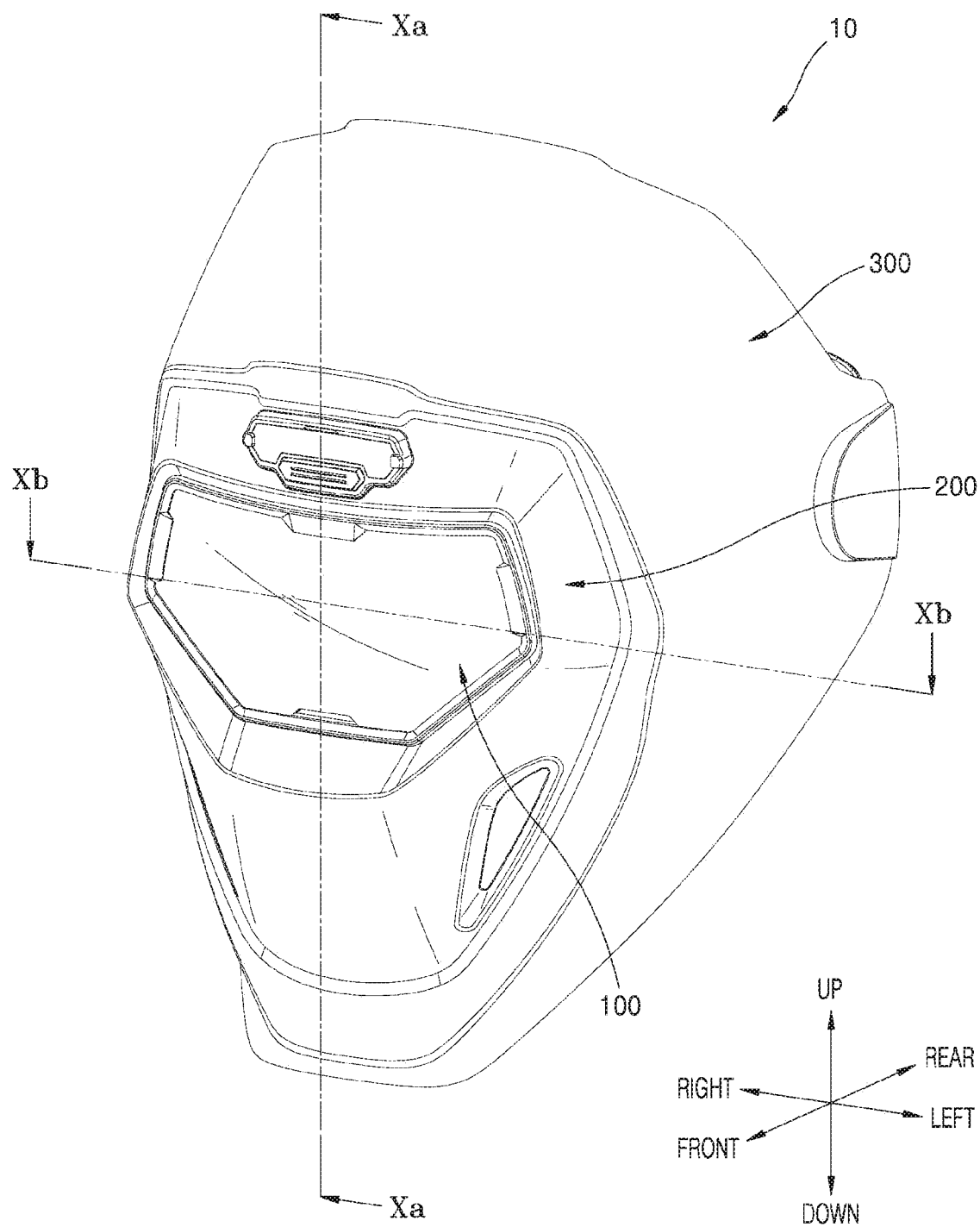
FIG. 1 is a schematic perspective view of a welder protector according to an embodiment.

As the disclosure allows for various changes and numerous embodiments, embodiments will be illustrated in the drawings and described in detail in the written description. However, this is not intended to limit the present disclosure to particular modes of practice, and it is to be appreciated that all changes, equivalents, and substitutes that do not depart from the spirit and technical scope of the present disclosure are encompassed in the present disclosure.

Hereinafter, reference will now be made in detail to embodiments, examples of which are illustrated in the accompanying drawings, wherein like reference numerals refer to like elements throughout and any redundant descriptions thereof are omitted.

In the description below, it will be understood that although the terms "first," "second," etc. may be used herein to describe various components, these components should not be limited by these terms. These components are only used to distinguish one component from another.

In the description below, as used herein, the singular forms "a," "an" and "the" are intended to include the plural forms as well, unless the context clearly indicates otherwise.

In the description below, it will be further understood that the terms "comprises" and/or "comprising" used herein specify the presence of stated features or components, but do not preclude the presence or addition of one or more other features or components.

In the description below, it will be understood that when a layer, region, or component is referred to as being "formed on" another layer, region, or component, it can be directly or indirectly formed on the other layer, region, or component. That is, for example, intervening layers, regions, or components may be present.

In the drawings, sizes of components in the drawings may be exaggerated for convenience of explanation. In other words, since sizes and thicknesses of components in the drawings are arbitrarily illustrated for convenience of explanation, the following embodiments are not limited thereto.

When a certain embodiment may be implemented differently, a specific process order may be performed differently from the described order. For example, two consecutively described processes may be performed substantially at the same time or performed in an order opposite to the described order.

In the description below, it will be understood that when a layer, region, or component is referred to as being "formed on" another layer, region, or component, it can be directly or indirectly formed on the other layer, region, or component. That is, for example, intervening layers, regions, or components may be present.

Figure 2:
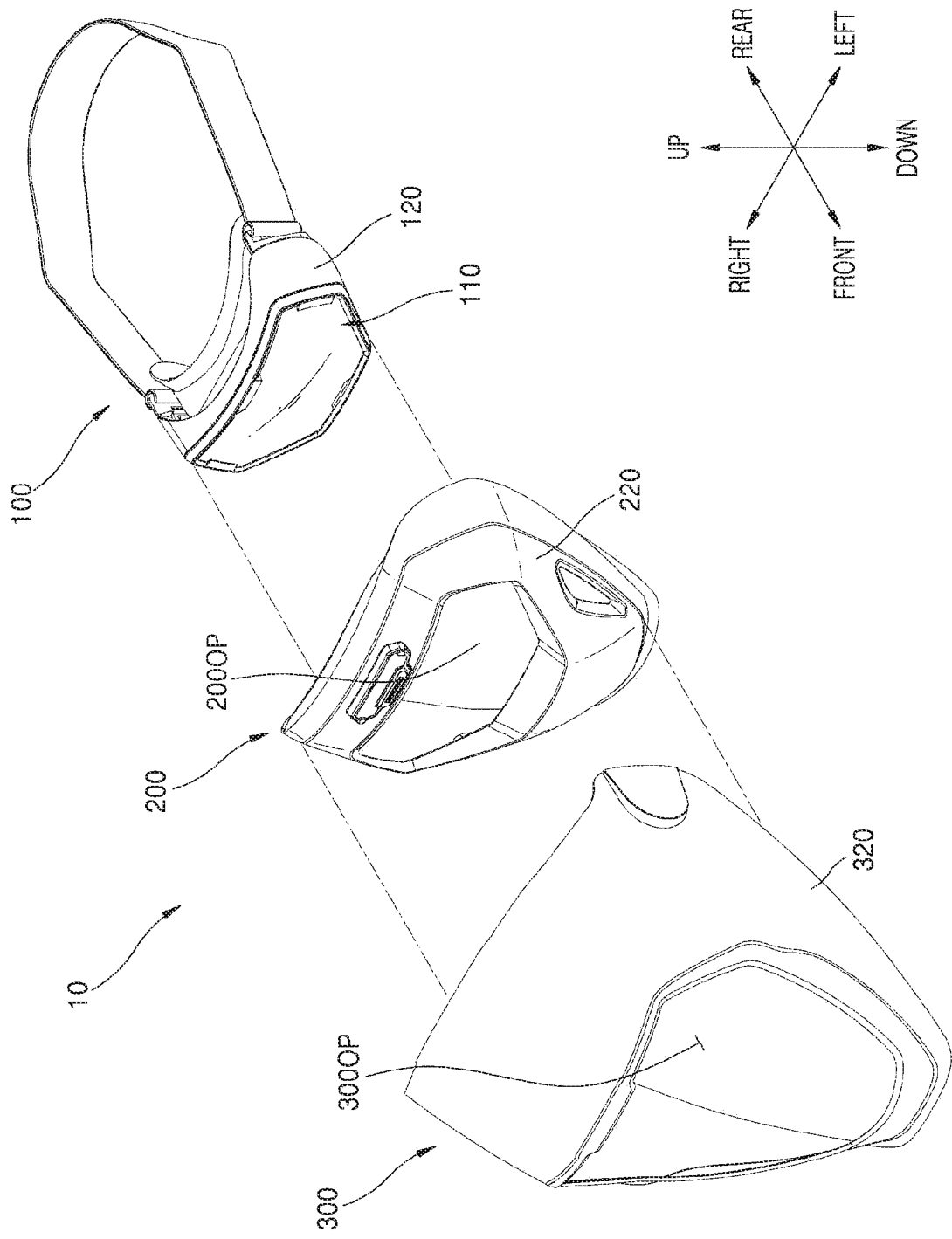
FIG. 2 is an exploded perspective view of a welder protector according to an embodiment.

FIG. 1 is a schematic perspective view of a protector (or welder protection device) 10 for welder according to an embodiment. FIG. 2 is an exploded perspective view of a welder protector according to an embodiment.

Referring to FIGS. 1 and 2, the welder protector 10 may include goggles 100, a face shield 200, and a helmet 300. The goggles 100, the face shield 200, and the helmet 300 of the welder protector 10 are structures that are combinable with and separable from each other. The welder protector 10 may selectively protect the worker's body according to the work content of the worker. For example, the welder protector 10 may selectively protect the eyes, a face including the eyes, or at least a part of a head including the face and the eyes, for example, the top of the head and the ear portion of the worker.

The goggles 100 may be selectively combined with and/or separable from the face shield 200. The goggles 100 may be connected to a frame 120 and may include a window portion 110 for visually providing a worker with an external situation. The face shield 200 may include a first opening 200OP corresponding to the window portion 110 of the goggles 100. The first opening 200OP may be defined by a shield surface part 220 of the face shield 200. The shield surface part 220 may completely surround the first opening 200OP at the edge of the first opening 200OP and have an area covering the lower part of the face (or jaw area of the face) and the forehead (or the upper part of the face) of a worker.

The goggles 100 may be coupled to the face shield 200 from the inner side to the outer side of the face shield 200, that is, from the rear side to the front side in FIG. 2. The window portion 110 of the goggles 100 may be exposed to the outside through the first opening 200OP. When the goggles 100 are solely worn by a worker, the goggles 100 may mainly protect the eyes of the face of a worker. However, when the goggles 100 are worn by a worker by being coupled to the face shield 200, the goggles 100 may protect the entire area of the face of a worker, including the eyes. The goggles 100 coupled to the face shield 200 may be separable from the face shield 200 according to the worker's choice.

A coupling structure of the goggles 100 and the face shield 200 may be selectively coupled to and/or separated from the helmet 300. The helmet 300 may include a second opening 300OP corresponding to the face shield 200. The second opening 300OP may be defined by a protection surface part 320 of the helmet 300. The protection surface part 320 may completely surround the second opening 300OP and have an area covering the top of the head and the ear portion of the worker. The second opening 300OP may overlap the first opening 200OP, but may be greater than the first opening 200OP.

The coupling structure of the goggles 100 and the face shield 200 may be coupled to the helmet 300 from the inner side to the outer side of the helmet 300, that is, from the rear side to the front side in FIG. 2. A part of the goggles 100 and the face shield 200, for example, a partial area of the shield surface part 220, may be exposed to the outside through the second opening 300OP. When the coupling structure of the goggles 100 and the face shield 200 is worn by the worker, the face of the worker, including the eyes, may be protected. However, when the above-described coupling structure that is coupled to the helmet 300 is worn by the worker, not only the face of the worker, but also a peripheral area of the face, for example, the ears and the top of the head, may be protected. The coupling structure coupled to the helmet 300 may be separated, according to the worker's choice, into the coupling structure of the goggles 100 and the face shield 200, or may be individually separated such as only the goggles 100 are separated from the helmet 300.

Figure 3:
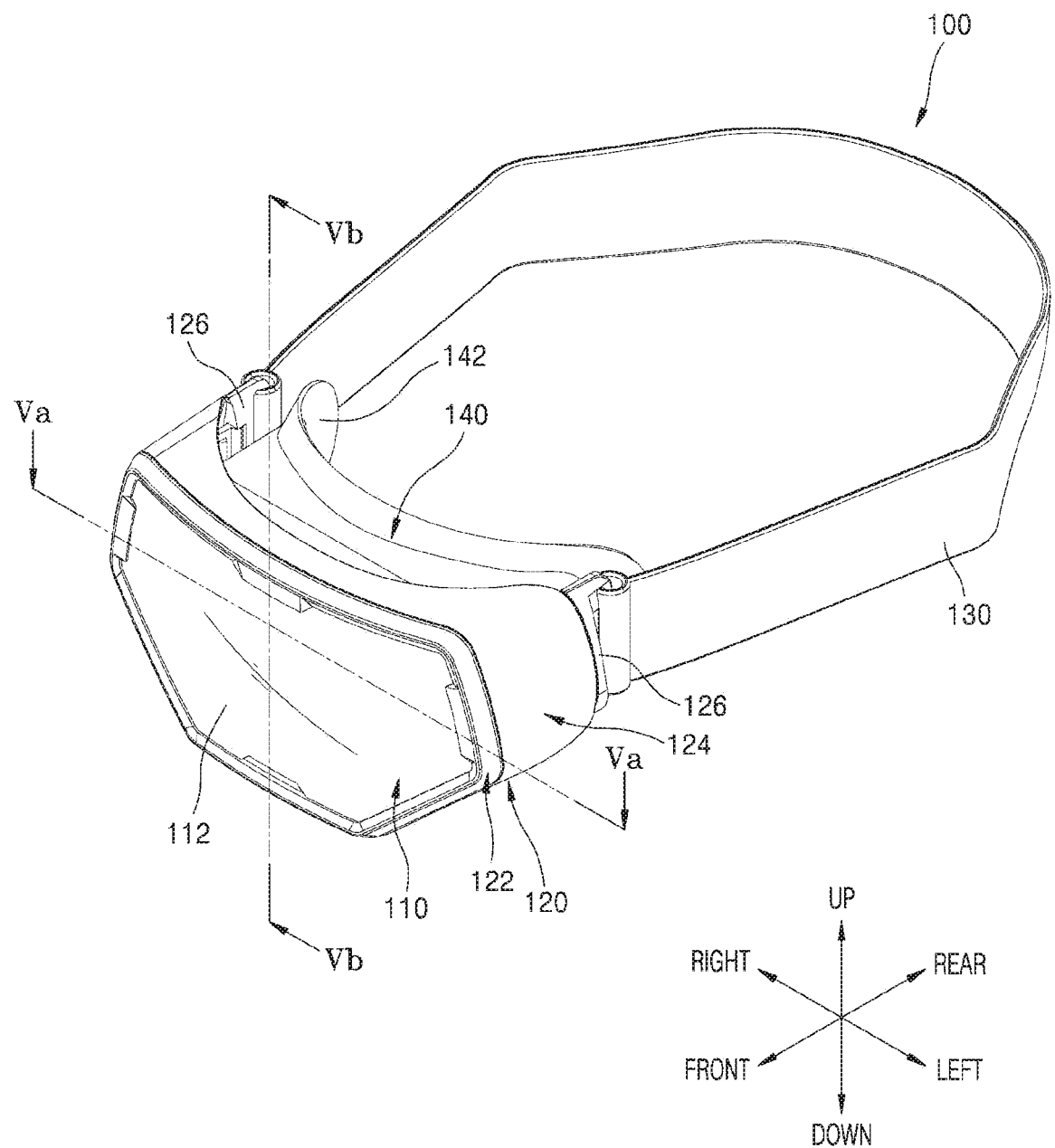
FIG. 3 is a perspective view of goggles according to an embodiment.
Figure 4:
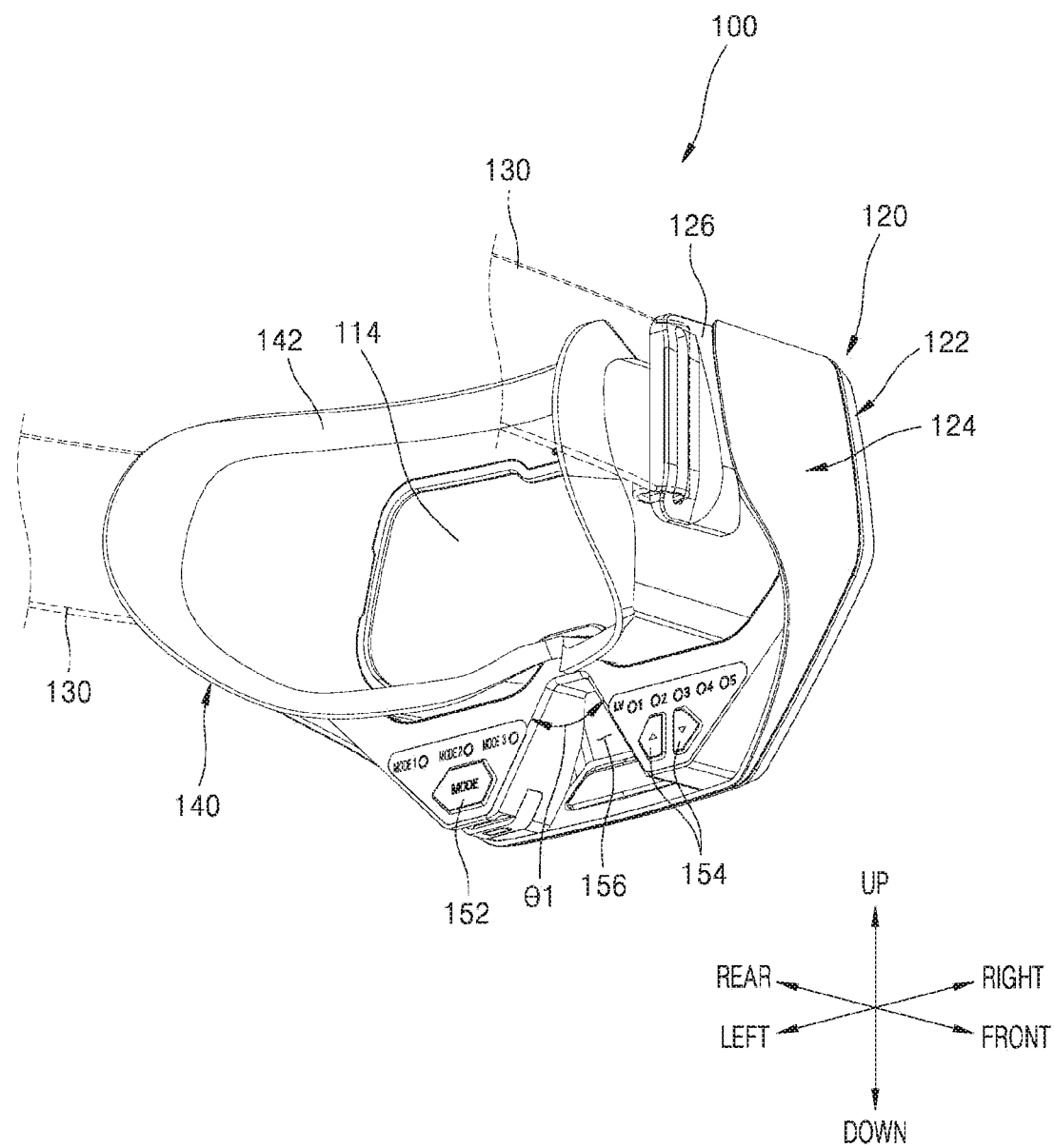
FIG. 4 is a perspective view of the goggles according of FIG. 3 viewed at a different angle.
Figure 5A:
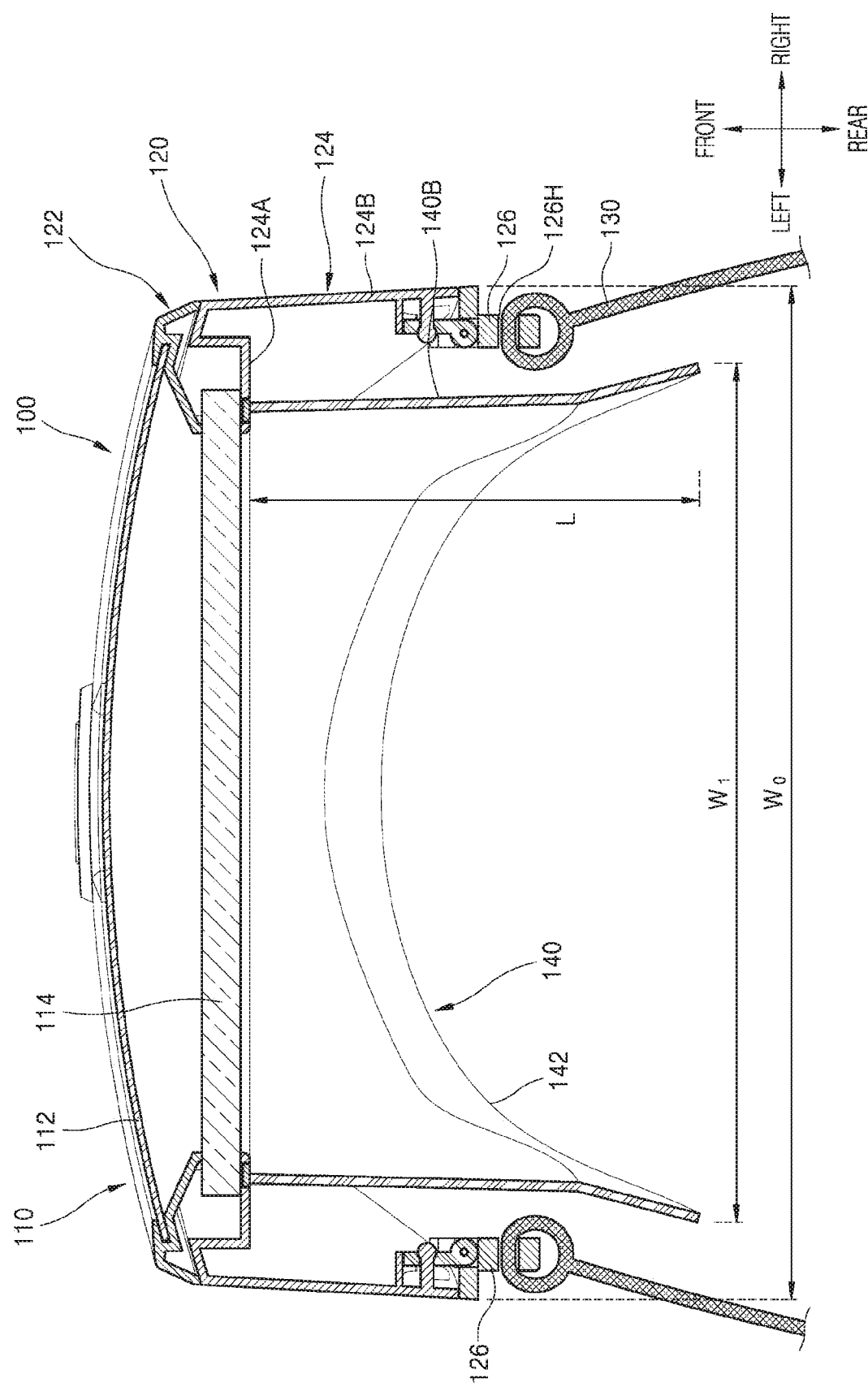
FIG. 5A is a cross-sectional view taken along line Va-Va of FIG. 3.
Figure 5B:
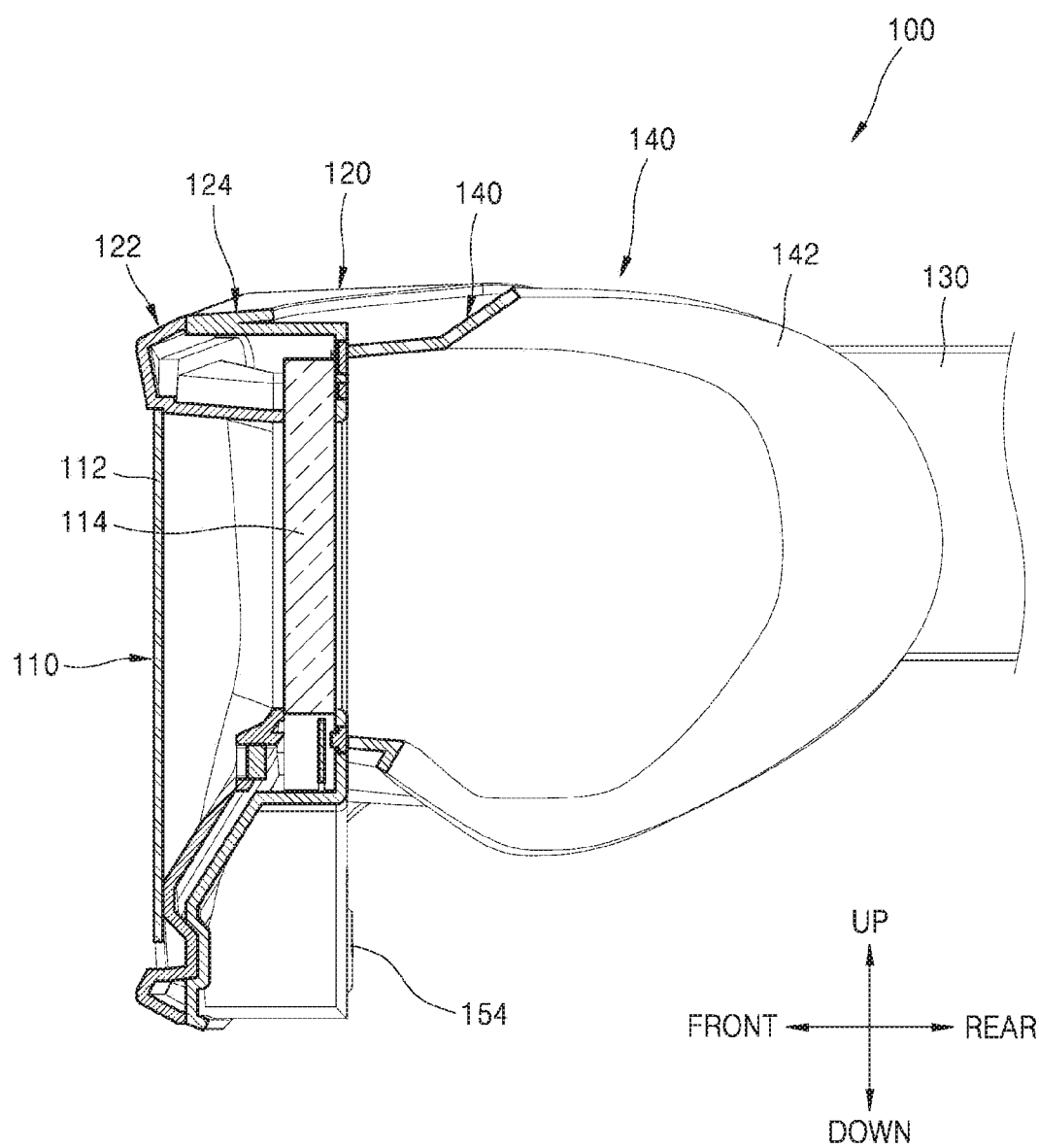
FIG. 5B is a cross-sectional view taken along line Vb-Vb of FIG. 3.

FIG. 3 is a perspective view of goggles according to an embodiment. FIG. 4 is a perspective view of the goggles according of FIG. 3 viewed at a different angle. FIG. 5A is a cross-sectional view taken along line Va-Va of FIG. 3. FIG. 5B is a cross-sectional view taken along line Vb-Vb of FIG. 3.

Referring to FIGS. 3 to 5B, the window portion 110 of the goggles 100 may be supported by the frame 120 and being coupled to the frame which is provided nearby the window portion 110. The window portion 110 may include a transparent substrate 112 located at the forefront side, and an electronic optical element 114 arranged spaced a certain distance apart from the transparent substrate 112. The transparent substrate 112 may include glass or resin material that transmits light. The electronic optical element 114 may include liquid crystal, and darkening of the electronic optical element 114 may be adjusted according to the orientation direction of liquid crystal of the electronic optical element 114.

The transparent substrate 112 and the electronic optical element 114 are connected to the frame 120. The transparent substrate 112 may be inserted into a front frame 122, and the position of the electronic optical element 114 located at the rear of the transparent substrate 112 may be fixed by a rear frame 124 connected to the front frame 122. The rear frame 124 may include a front portion 124A supporting the electronic optical element 114 between the front frame 122 and the rear frame 124, and a side portion 124B extending on another plane to cross the front portion 124A and forming the side portion of the goggles 100. The side portion 124B extends toward the rear side. Referring to FIGS. 5A and 5B, the front frame 122 and the rear frame 124 of the frame 120 are individually formed such that one element is inserted in another element to be coupled thereto.

An extension member 140 that is optically connected to the window portion 110 and extends to the rear side may be arranged in the goggles 100. The extension member 140, as illustrated in FIG. 5A, may have a width $W_1$ that is less than a width $W_0$ of the frame 120. The extension member 140, as illustrated in FIG. 5A, may have a length L extending to the rear side further than the frame 120 passing an end portion of the frame 120, for example, an end portion of the side portion 124B. A side portion 140B of the extension member 140 may be arranged spaced a certain distance apart from the side portion 124B of the frame 120.

The extension member 140 may have a shape like a tube that optically and/or spatially connects the eyes of a worker wearing the goggles 100 and the window portion 110. An end surface 142 of the extension member 140 may closely or directly contact the face of a worker. The end surface 142 may extend to surround the eyes of a worker and include an inclined surface that externally spreads out.

An image perceived by the worker through the window portion 110 may proceed toward the eyes of a worker through a space defined by the extension member 140, for example, a space surrounded by the side portion 140B of the extension member 140, and the end surface 142 closely contacts the face, thereby preventing external light, for example, a flame of strong intensity generated during welding, from proceeding toward the eyes of a worker. Accordingly, a worker may easily check the image provided through the window portion 110 without being affected by the surrounding environment. The extension member 140, as illustrated in FIG. 5B, may be formed separate from the rear frame 124 and then connected to the frame 120 such that a part of the extension member 140 is inserted in a hole of the frame 120. The extension member 140 may include a different material from the material of the frame 120. For example, the end surface 142 of the extension member 140 or a portion including the end surface 142 may include a material that does not damage the skin of a worker, for example, polymer such as silicone or/and urethane-based resin. The extension member 140 may include porous polymer, but the present disclosure is not limited thereto.

A wearing portion 130 is an element to fix the goggles 100 to the head of a worker when wearing the goggles 100, and may be connected to the frame 120 through a coupling piece 126. Referring to FIGS. 3 and 4, an end portion of the wearing portion 130 is inserted into a hole 126H of the coupling piece 126 located at a rear end of the rear frame 124. The wearing portion 130 may include a band type that is formed of an elastic material and has an adjustable length, but the present disclosure is not limited thereto. The wearing portion 130 may include length-adjustable gear and may be adjusted to the size of the head of a worker through a relative movement of the gear.

The goggles 100, as illustrated in FIG. 4, may include first and second operation portions 152 and 154 therein. The first and second operation portions 152 and 154 may be located at the rear side of the window portion 110. For example, the first and second operation portions 152 and 154 may be arranged spaced apart from each other with a space (or a notch part) 156 for accommodating the nose of a worker therebetween. The space 156 may have a fan shape having a first angle θ1 to correspond to the nose of a worker.

For example, among the first and second operation portions 152 and 154, the first operation portion 152 may be used to select one of a plurality of modes and the second operation portion 154 may be used to change a level. The modes may be related to settings needed for welding work, such as a sending mode, a darkening mode, or a delay mode. The level may be related to a degree or intensity in a particular mode. For example, when a darkening mode is set through the first operation portion 152, a degree of darkening may be controlled by the second operation portion 154.

Figure 6:
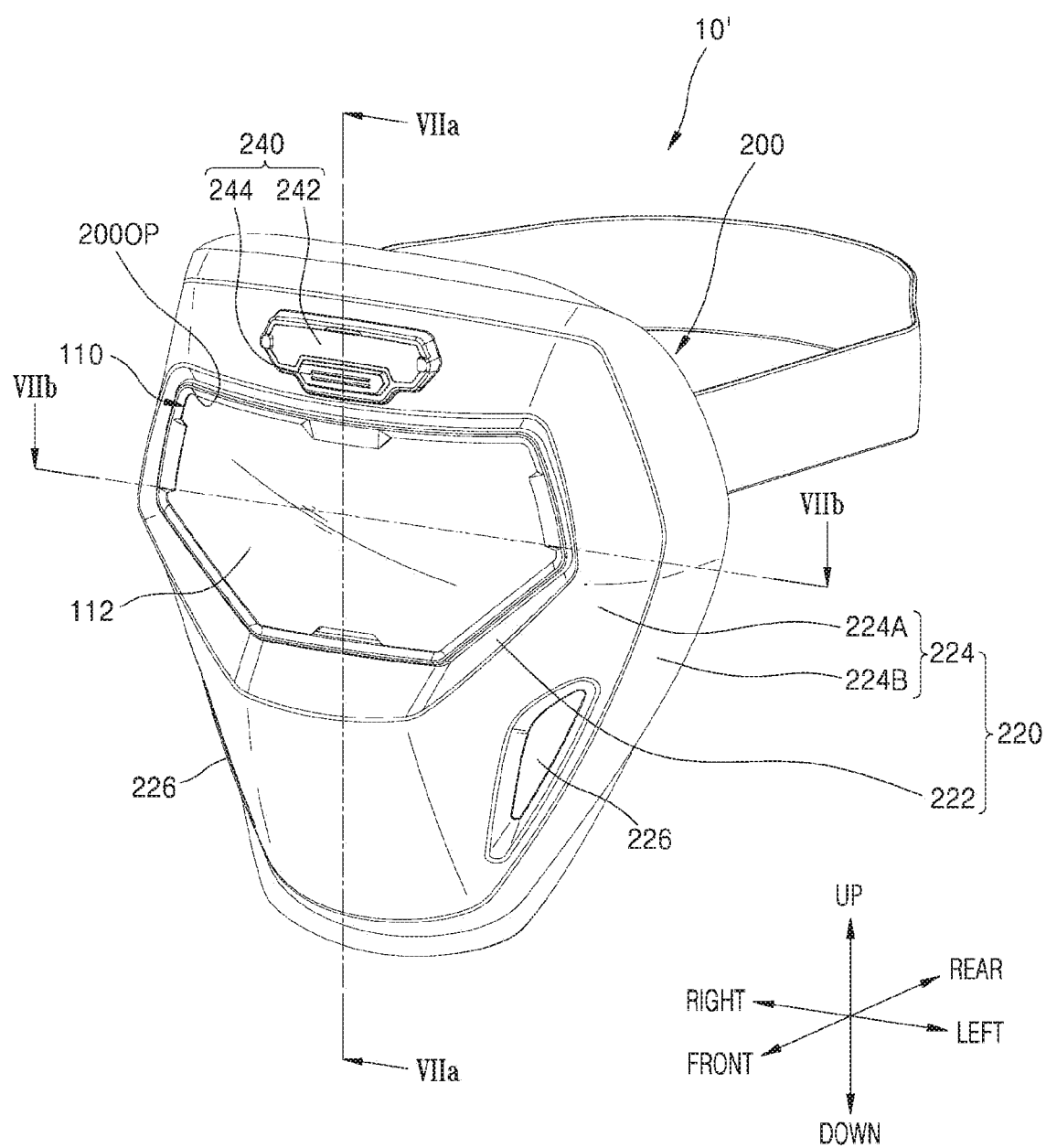
FIG. 6 is a perspective view illustrating a state in which the goggles and the face shield of FIG. 1 are coupled to each other.
Figure 7B:
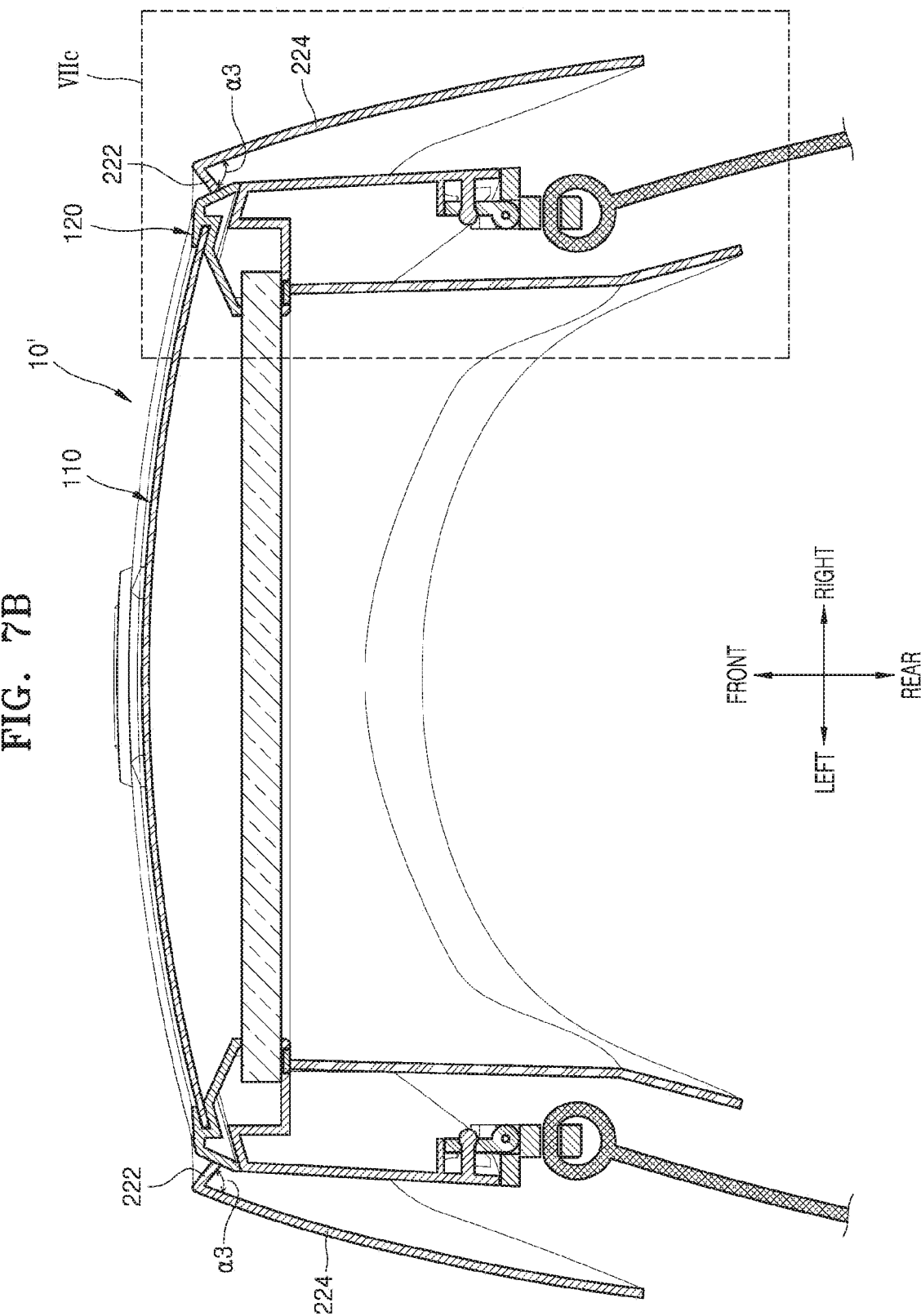
FIG. 7B is a cross-sectional view taken along line VIIb-VIIb of FIG. 6.
Figure 7C:
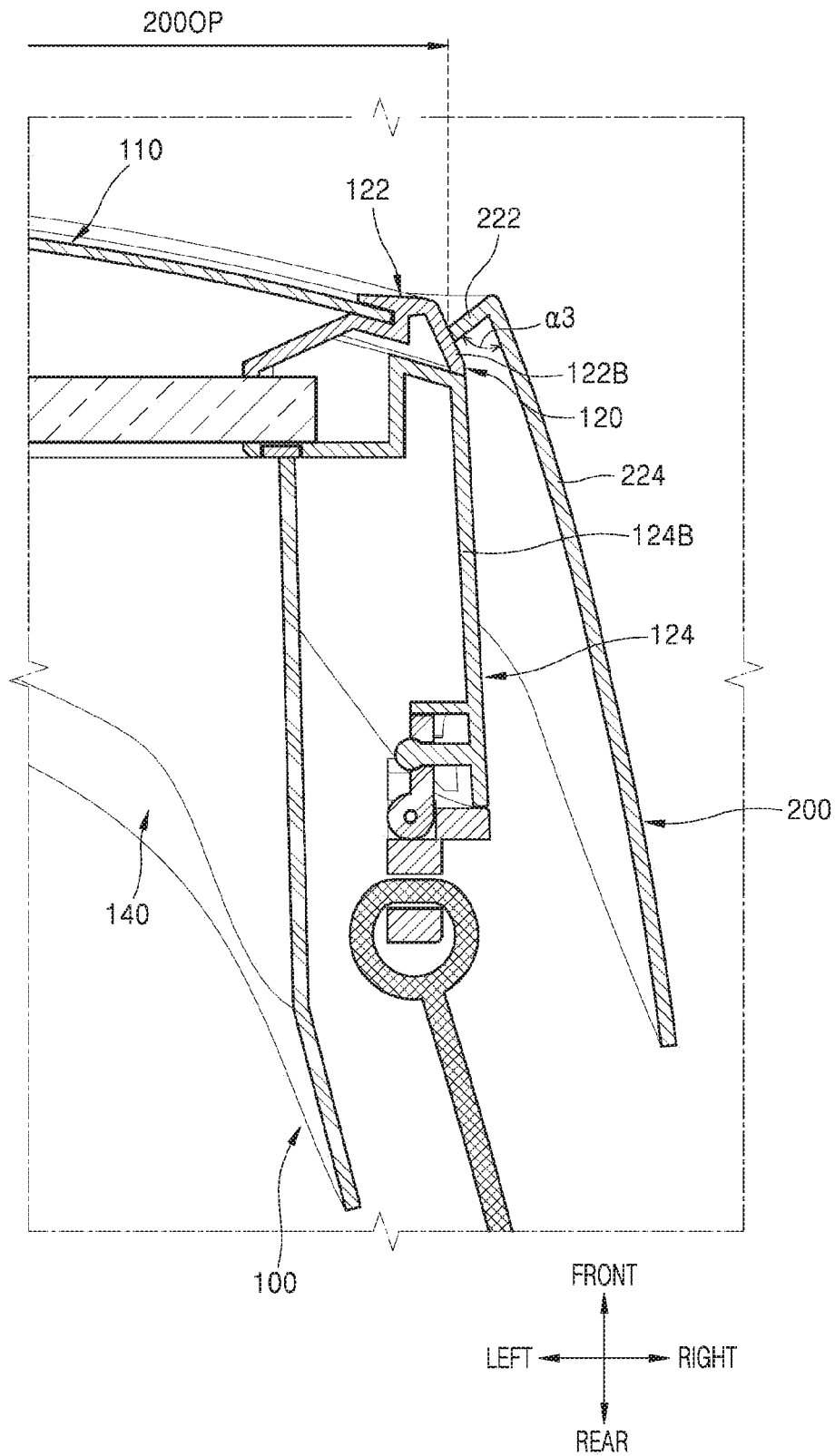
FIG. 7C is an enlarged view of a portion VIIc of FIG. 7B.

FIG. 6 is a perspective view illustrating a state in which the goggles 100 and the face shield 200 of FIG. Tare coupled to each other. FIG. 7A is a cross-sectional view taken along line VIIa-VIIa of FIG. 6. FIG. 7B is a cross-sectional view taken along line VIIb-VIIb of FIG. 6. FIG. 7C is an enlarged view of a portion VIIc of FIG. 7B.

Referring to FIGS. 6 to 7B, the goggles 100 of a welder protector 10' is coupled to the face shield 200 by being inserted from the inside to the outside of the face shield 200, as described above, and the window portion 110 of the goggles 100 is exposed through the first opening 200OP. The first opening 200OP is defined by an inner edge of the shield surface part 220. The shield surface part 220 of the face shield 200 may include a main surface part 224 that covers the side portion of the goggles 100.

The main surface part 224 is a portion defining the shape and area of the face shield 200, and may cover the forehead and the lower part of a face of a worker. A light-emitting portion 240 may be arranged on the main surface part 224. The light-emitting portion 240 may emit certain light to secure visibility of a worker in a dark environment and may include a light-emitting body 242, such as an LED, and a button 244 for controlling turning on/off of the light-emitting body 242. The main surface part 224 may include a plurality of recessed portions 226 spaced a certain distance apart from each other. The recessed portions 226 are areas for control by a worker using a hand during an operation such as separating or removing the face shield 200 from the face of a worker. The recessed portions 226 may be respectively arranged at positions corresponding to both cheeks of a worker.

In an embodiment, the main surface part 224 may include a first main surface part 224A extending from the edge of the first opening 200OP to surround the first opening 200OP and a second main surface part 224B surrounding the first main surface part 224A at the outer edge of the first main surface part 224A. At least a portion of the second main surface part 224B, as illustrated in FIGS. 6 and 7A, may have a surface crossing a surface of the first main surface part 224A. A bent portion (hereinafter, a boundary) between the first main surface part 224A and the second main surface part 224B may form a certain outline, but the present disclosure is not limited thereto. In another embodiment, the main surface part 224 may have a round shape overall. Accordingly, the boundary between the first main surface part 224A and the second main surface part 224B, that is, the outline, may not be formed.

The shield surface part 220 may include a bent surface part 222 having a certain area and located between the first opening 200OP and the main surface part 224. The bent surface part 222 may have a bent shape from the main surface part 224 forming a certain angle with the main surface part 224, and an end portion of the inner edge of the bent surface part 222 may correspond to the edge of the first opening 200OP. Internal angles α1, α2, and α3 formed between the main surface part 224 and the bent surface part 222 may have a value less than 180°, as illustrated in FIGS. 7A, 7B, and 7C. In FIG. 7A, the internal angles α1 and α2 between the first main surface part 224A and the bent surface part 222 have a value greater than 90° and less than 180°, and in FIG. 7B, the internal angles α1 and α2 between the first main surface part 224A and the bent surface part 222 may have a value less than 90°.

Referring to FIG. 7C, in detail, the bent surface part 222 may be bent from the main surface part 224 by a certain angle α3 to contact a first surface part (or a first side part) 122B of the goggles 100. When the goggles 100 and the face shield 200 are coupled to each other, the first surface part 122B of the goggles 100 and the bent surface part 222 of the face shield 200 contact each other around the first opening 200OP, and the goggles 100 may no longer proceed forward and may be coupled to the face shield 200 at a corresponding position.

The first surface part 122B of the goggles 100 may have a shape extending further backward from the contact portion with the bent surface part 222 and spreading out. For example, the first surface part 122B may extend backward passing the contact portion between the first surface part 122B and the bent surface part 222, and may have a shape having a width increasing in the up and down directions or the left and right directions. Accordingly, when the goggles 100 are coupled to the face shield 200 in a direction from the rear side to the front side, a coupling line or contact line between the goggles 100 and the first opening 200OP may be stably formed.

The main surface part 224, for example, a portion of the main surface part 224 corresponding to the side portion 124B of the goggles 100, is arranged a certain distance spaced apart from the side portion 124B, and thus unnecessary interference during the coupling of the goggles 100 and the face shield 200 may be removed. A spatial separation between the side portion 124B of the goggles 100 and the main surface part 224 of the face shield 200 may be structurally determined by the bent surface part 222 of the face shield 200 having a certain length or/and an extension angle of the main surface part 224 with respect to the bent surface part 222.

Figure 8A:
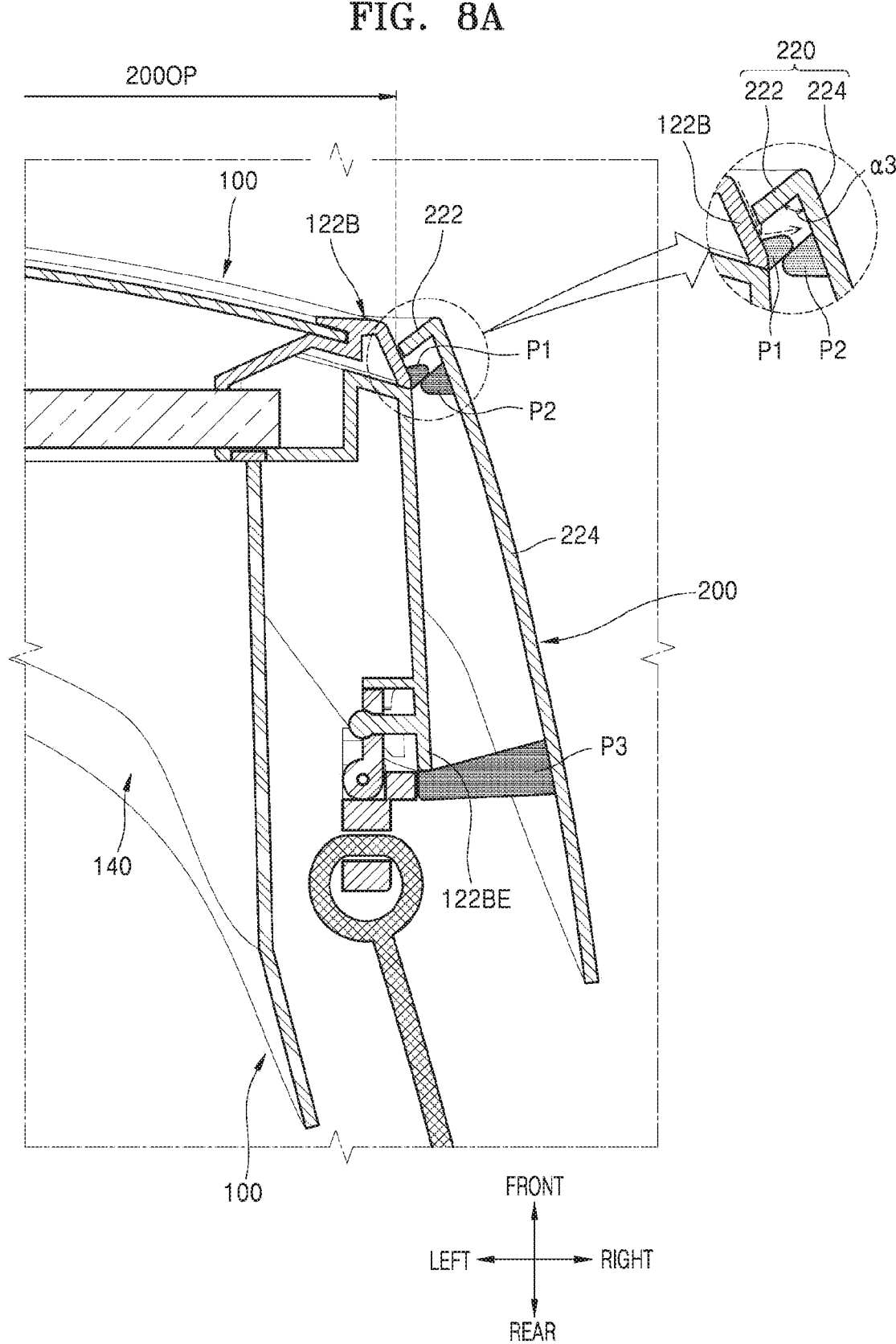
FIGS. 8A and 8B are cross-sectional views illustrating a state in which the goggles and the face shield are coupled to each other, in a welder protector according to another embodiment.
Figure 8B:
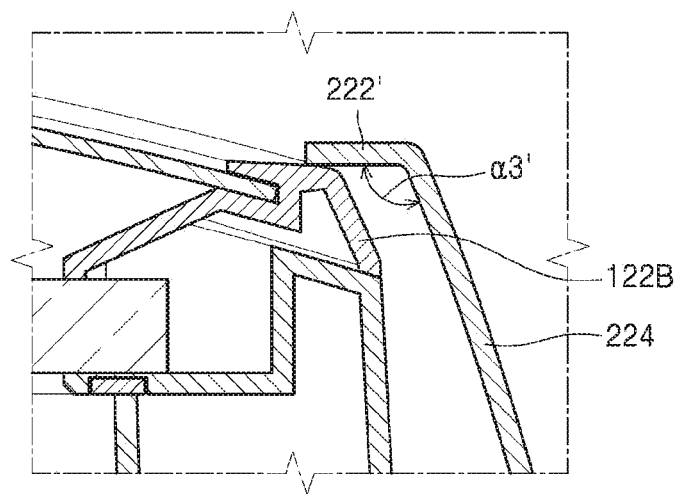

FIGS. 8A and 8B are cross-sectional views illustrating a state in which the goggles 100 and the face shield 200 are coupled to each other, in a welder protector according to another embodiment.

Referring to FIG. 8A, a first protrusion P1 may be provided in an inner space between the goggles 100 and the face shield 200 and adjacent to the first opening 200OP. The first protrusion P1 may protrude from the first surface part 122B of the goggles 100 to cover a fine gap between the first surface part 122B of the goggles 100 and the bent surface part 222 of the face shield 200.

As the goggles 100 and the face shield 200 have a detachable coupling structure, a fine gap may be formed along an edge line of the first opening 200OP, for example, a coupling line between the goggles 100 and the face shield 200. For example, as shown by a dashed arrow illustrated in an enlarged view of a portion of FIG. 8A, light, fumes, or spatter generated during welding may intrude through the fine gap between the first surface part 122B of the goggles 100 and the bent surface part 222 of the face shield 200. As the first protrusion P1 at least partially covers the gap, the intrusion of the above materials may be prevented, or/and a path through which the above materials are intruded may be is extended. Thus, the intrusion of the above materials may be prevented or reduced. In another embodiment, the first protrusion P1 may be disposed closer to the fine gap and may contact the bent surface part 222. In this case, the effect of the above materials on a worker may be further reduced and simultaneously a contact area between the goggles 100 and the face shield 200 is increased and thus the coupling therebetween may be kept stable.

The first protrusion P1 may include the same material as the material of the first surface part 122B of the goggles 100, or may be formed of a different material from the material of the first surface part 122B. When the first protrusion P1 and the first surface part 122B are formed of the same material, for example, the first protrusion P1 may be formed by increasing the thickness of a part of the first surface part 122B.

A second protrusion P2 may be provided in the inner space between the goggles 100 and the face shield 200 and adjacent to the first opening 200OP. When the face shield 200 and the goggles 100 are coupled to each other, the second protrusion P2 contacts the first protrusion P1, and thus a coupling force between the face shield 200 and the goggles 100 may be increased. For example, when the goggles 100 and the face shield 200 are coupled to each other, the first protrusion P1 passes the second protrusion P2 to be located between the bent surface part 222 and the second protrusion P2. Unless a force greater than a certain force pulling the goggles 100 back is applied, even when a relatively small impact is applied, the first protrusion P1 may be located between the bent surface part 222 and the second protrusion P2 while contacting the second protrusion P2.

The second protrusion P2 may protrude from an inner side surface of the face shield 200 and may be formed of the same material as the material of the shield surface part 220 of the face shield 200 or a different material from the material of the shield surface part 220. When the second protrusion P2 and the shield surface part 220 are formed of the same material, for example, the second protrusion P2 may be formed by increasing the thickness of a part of the shield surface part 220.

A third protrusion P3 may be provided inside the shield surface part 220 and may support the side portion of the goggles 100, for example, the frame 120. The third protrusion P3 may protrude from the inner side surface part of the face shield 200 and contact a rear end portion the frame 120 of the goggles 100 while supporting the goggles 100. In an embodiment, an end portion of the third protrusion P3 may have a hook shape bent to contact the inside of the rear end portion 122BE of the frame 120.

Each of the first to third protrusions P1, P2, and P3 may have a loop shape extending long along the coupling line of the goggles 100 and the face shield 200. In an embodiment, one or more of the first to third protrusions P1, P2, and P3 may extend along the coupling line of the goggles 100 and the face shield 200, and surround, for example, the overall edge of the window portion 110. Alternatively, one or more of the first to third protrusions P1, P2, and P3 may have a plurality of sub-protrusions that are arranged spaced a certain distance apart from each other and extend along the coupling line of the goggles 100 and the face shield 200.

Although FIG. 8A illustrates that all of the first to third protrusions P1, P2, and P3 are provided, the present disclosure is not limited thereto. In embodiments derived from the above-described embodiments, at least one of the first to third protrusions P1, P2, and P3 may be provided.

Although FIG. 8A illustrates that the bent surface part 222 contacts an outer surface of the first surface part 122B such that the angle α3 between the bent surface part 222 and the main surface part 224 is 90° or less, the present disclosure is not limited thereto. In another embodiment, as illustrated in FIG. 8B, a bent surface part 222' may contact the first surface part 122B by being bent with respect to the main surface part 224 such that an internal angle α3' between the bent surface part 222' and the main surface part 224 is obtuse angle. Although not illustrated in FIG. 8B, the embodiment of FIG. 8B and embodiments derived therefrom may further include at least one protrusion selected from among the first to third protrusions P1, P2, and P3.

Figure 9:
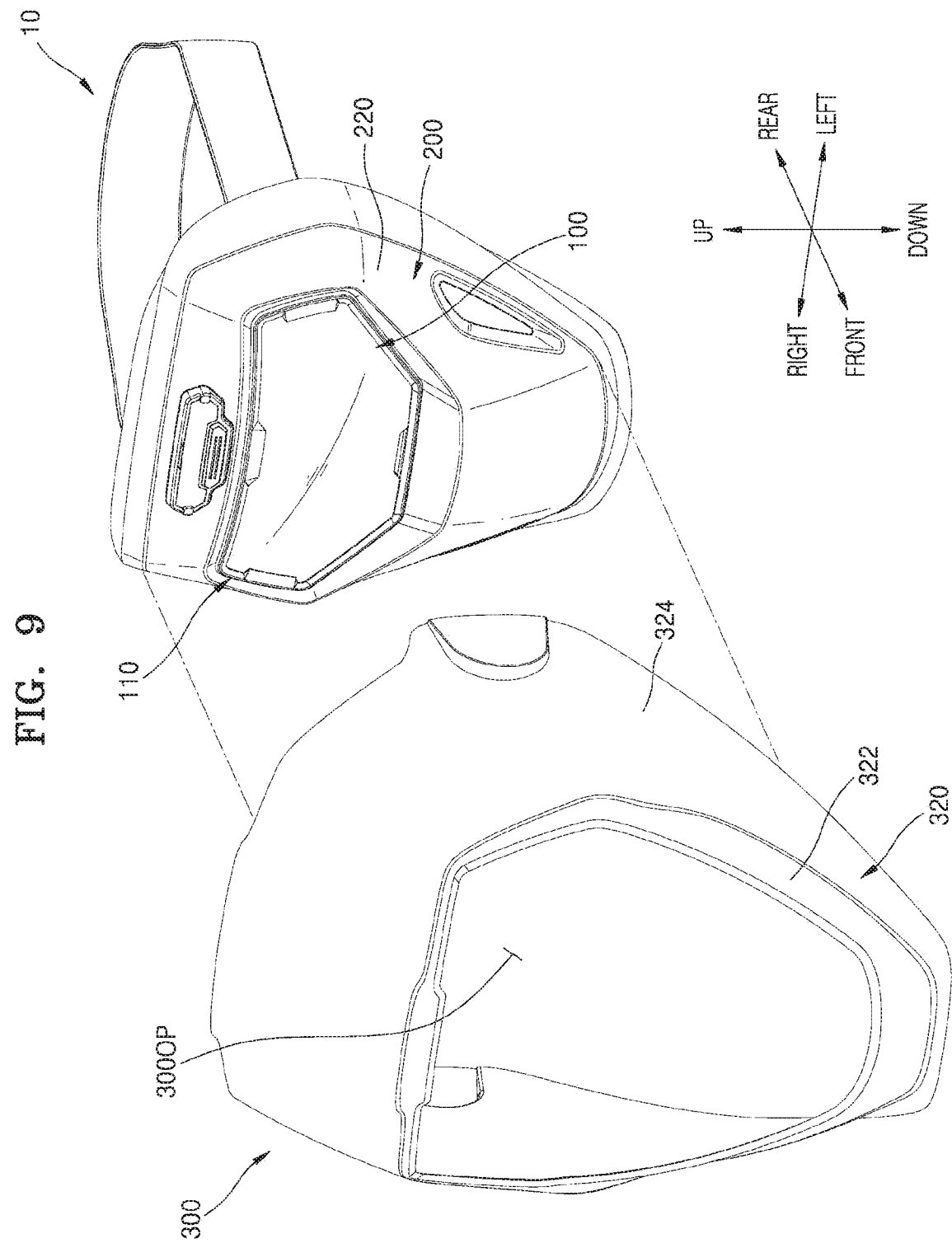
FIG. 9 is an exploded perspective view of a helmet and a structure in which the goggles and the face shield are coupled to each other, in a welder protector according to another embodiment.
Figure 10A:
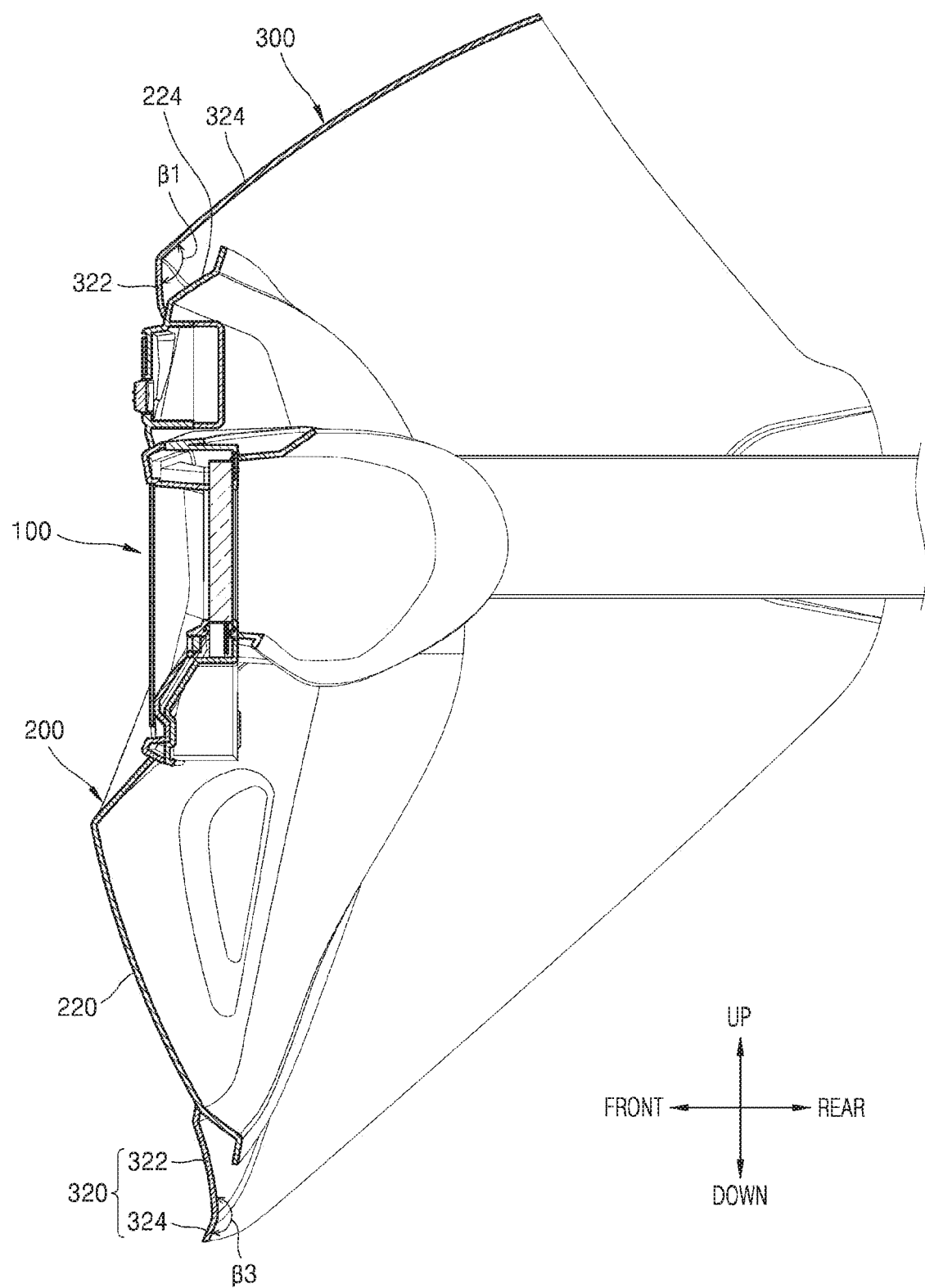
FIG. 10A is a cross-sectional view taken along line Xa-Xa of FIG. 1.

FIG. 9 is an exploded perspective view of a helmet and a structure in which the goggles and the face shield are coupled to each other, in a welder protector according to another embodiment. FIGS. 10A and 10B are cross-sectional views of a state in which the structure of FIG. 9 and the helmet are coupled to each other, in which FIG. 10A is a cross-sectional view taken along line Xa-Xa of FIG. 1 and FIG. 10B is a cross-sectional view taken along line Xb-Xb of FIG. 1.

Referring to FIGS. 9 to 10B, the coupling structure of the goggles 100 and the face shield 200 may be coupled to the helmet 300 by being inserted from the inside to the outside of the helmet 300. The window portion 110 of the goggles 100 and a part of the shield surface part 220 of the face shield 200 are exposed through the second opening 300OP. The helmet 300 may include the protection surface part 320 surrounding the second opening 300OP. The second opening 300OP is defined by an inner edge of the protection surface part 320.

The protection surface part 320 is a portion defining the shape and area of the helmet 300, and may cover the top of the head and the ear portion of a worker. The protection surface part 320 may include a main surface part 324 and a bent surface part 322 bent by a certain angle with respect to the main surface part 324. An end portion of the inner edge of the bent surface part 322 may correspond to an edge of the second opening 300OP.

The bent surface part 322, as illustrated in FIGS. 10A and 10B, may have internal angles β1 and β2 with the main surface part 324, each of the internal angles β1 and β2 having a value less than 180°. An area of the lower side of the bent surface part 322 may have an internal angle β3 greater than 180° with the main surface part 324. Accordingly, when wearing the helmet 300, a worker may not feel uncomfortable.

The bent surface part 322 may be bent from the main surface part 324 forming a certain angle, and a partial region of the bent surface part 322 may be bent at least once. FIGS. 10A and 10B illustrate that the bent surface part 322 includes a region that is bent once before contacting the face shield 200.

The bent surface part 322 may contact the shield surface part 220 of the face shield 200. When the coupling structure of the goggles 100 and the face shield 200 is coupled to the helmet 300, the coupling structure no longer proceeds forward and may be coupled to the helmet 300 while the bent surface part 322 and the shield surface part 220 contact each other.

A portion of the face shield 200, for example, the main surface part 224, may have a shape that further extends backward from a contact portion between the bent surface part 322 of the helmet 300 and the shield surface part 220 and gradually spreads out. As illustrated in FIGS. 10A and 10B, the main surface part 224 of the face shield 200 may have a shape that extends backward passing the contact portion and has a width increasing in the up and down directions or the left and right directions. Accordingly, when the coupling structure proceeding from the rear side to the front side and the helmet 300 are coupled to each other, a coupling line (contact line) of the shield surface part 220 and the second opening 300OP may be stably formed.

As the main surface part 324 of the protection surface part 320 of the helmet 300 is arranged spaced a certain distance apart from the shield surface part 220 of the face shield 200, unnecessary interference during the coupling between the coupling structure and the helmet 300 may be removed. For example, an edge portion of the protection surface part 320 and an edge portion of the shield surface part 220 arranged inside the coupling line of the helmet 300 and the face shield 200 may be arranged spaced apart from each other. The separation therebetween may be determined by the bending structure of the protection surface part 320 and the bending structure of the shield surface part 220.

Figure 11:
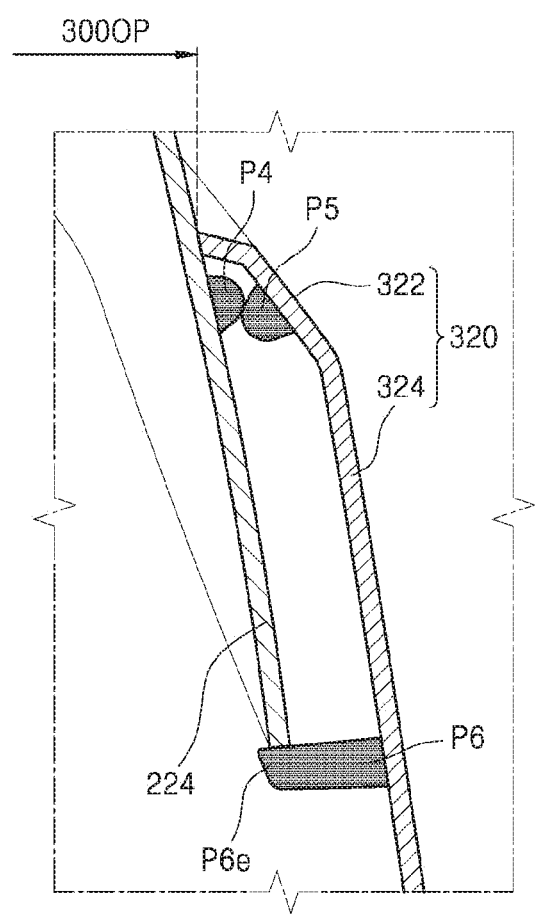
FIG. 11 is a cross-sectional view of a part of a welder protector according to another embodiment.

FIG. 11 is a cross-sectional view of a part of a welder protector according to another embodiment, which corresponds to a modified embodiment of a portion 'A' of FIG. 10B.

Referring to FIG. 11, a fourth protrusion P4 may be provided in an inner space between the face shield 200 and the helmet 300 and adjacent to the second opening 300OP. The fourth protrusion P4 may protrude from the main surface part 224 of the face shield 200 to at least partially cover the edge line of the second opening 300OP, for example, a fine gap between the main surface part 224 of the face shield 200 and the bent surface part 322 of the helmet 300. Accordingly, light, fumes, or spatter that may intrude through the fine gap may be prevented or an intrusion path may be increased.

The fourth protrusion P4 may be integrally formed of the same material as the material of the main surface part 224 of the face shield 200, or may be formed of a different material from the material of the main surface part 224. When the fourth protrusion P4 and the main surface part 224 are formed of the same material, the fourth protrusion P4 may be formed by increasing the thickness of a part of the main surface part 224.

A fifth protrusion P5 may be further arranged in the inner space between the face shield 200 and the helmet 300 and adjacent to the second opening 300OP. During the coupling of the coupling structure and the helmet 300, the fourth protrusion P4 may pass the fifth protrusion P5, and after the coupling of the coupling structure and the helmet 300, as the fourth protrusion P4 and the fifth protrusion P5 contact each other, the separation of the coupling structure and the helmet 300 due to an external impact may be prevented or reduced. The fifth protrusion P5 may be arranged inside the protection surface part 320 of the helmet 300 and may protrude from the protection surface part 320 toward the inner space. The fifth protrusion P5 may be integrally formed of the same material as the material of the protection surface part 320 of the helmet 300 or formed of a different material from the material of the protection surface part 320.

The sixth protrusion P6 may be arranged inside the protection surface part 320 of the helmet 300 and may support a rear end portion 220E of the shield surface part 220 of the face shield 200. Although not illustrated, an end portion P6e of the sixth protrusion P6 may have a hook shape.

Although FIG. 11 illustrates that the fourth to sixth protrusions P4, P5, and P6 are all provided, the present disclosure is not limited thereto. A variety of modifications may be possible such that at least one selected from among the fourth to sixth protrusions P4, P5, and P6 is provided.

Each the fourth to sixth protrusions P4, P5, and P6 may extend long along the coupling line of the face shield 200 and the helmet 300. In an embodiment, one or more of the fourth to sixth protrusions P4, P5, and P6 may extend along the coupling line of the face shield 200 and the helmet 300 and may have a loop shape surrounding, for example, the edge of the second opening 3000P overall. Alternatively, one or more of the fourth to sixth protrusions P4, P5, and P6 may have a plurality of sub-protrusions that are arranged spaced a certain distance apart from each other and extend along the coupling line of the face shield 200 and the helmet 300.

As described above, in the welder protector according to the embodiments of the present disclosure, constituent elements forming the welder protector may be easily detachable according to the worker's choice, and various parts of the body may be protected through various combinations of the elements of the welder protector, by spatially separating the body of a worker from the external environment, for example, a welding environment. The above-described effects are exemplary, and other effects may be obtained from the present disclosure.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A welder protector for protecting a worker, comprising:
a face shield including a first opening and a shield surface part surrounding the first opening, the face shield having a front shield surface and a rear shield surface, the front shield surface being configured to face away from the worker when being worn by the worker;
goggles detachably coupled with the rear shield surface of the face shield and including a window portion, a frame that is configured to couple with the face shield, an extension member positioned inward of the frame, and a wearing portion, the window portion corresponding to the eyes of the worker, the wearing portion configured to extend at least partially around a head of the worker to secure the goggles on the head of the worker, wherein a goggles protrusion extends laterally outward from a laterally outward facing surface of the goggles; and
a helmet detachably coupled to the face shield and including a second opening corresponding to the face shield, wherein:
the shield surface part of the face shield comprises a main surface part covering a side portion of the goggles and a bent surface part bent toward the first opening from the main surface part to form an angle with the main surface part;
the shield surface part comprises a face shield protrusion that extends laterally inward from the main surface part;
the extension member comprises an end portion that is configured to contact the face of the worker and prevent external light from proceeding towards the eyes of the worker, the end portion extending in a rearward direction beyond a rear end of the frame;
the helmet comprises a front helmet surface and a rear helmet surface, the front helmet surface being configured to face away from the worker when being worn by the worker;
the front shield surface is coupled with the rear helmet surface when the helmet is coupled with the face shield;
when the goggles and the face shield are coupled to each other, distal ends of the goggles protrusion and the face shield protrusion extend beyond one another in generally opposite directions and the goggles protrusion is disposed between the bent surface part and the face shield protrusion so as to maintain engagement between the goggles and the face shield;
when the goggles, the face shield, and the helmet are coupled to each other, the window portion of the goggles is exposed through the second opening of the helmet; and
when the goggles and the face shield are coupled to each other, the wearing portion of the goggles is configured to secure both the goggles and the face shield on the head of the worker.

2. The welder protector of claim 1, wherein, when the goggles and the face shield are coupled to each other, a first surface part of the goggles provided around the window portion contacts an inner edge of the shield surface part, the inner edge defining the first opening.

3. The welder protector of claim 2,
wherein, when the goggles and the face shield are coupled to each other, the face shield protrusion is adjacent to an edge of the first opening and is arranged in an inner space between the goggles and the face shield.

4. The welder protector of claim 3, wherein the goggles protrusion protrudes from the laterally outward-facing surface to at least partially cover a contact portion between the first surface part of the goggles and an inner edge of the face shield.

5. The welder protector of claim 1, wherein the goggles comprise a transparent substrate and an electronic optical element that is disposed inside the transparent substrate and comprises liquid crystal.

6. The welder protector of claim 1, wherein the helmet comprises a protection surface part surrounding the second opening, and
the face shield is coupled to the helmet by proceeding from the inside of the helmet toward the second opening such that the shield surface part contacts an inner edge of the protection surface part.

7. The welder protector of claim 1, wherein when the goggles, the face shield, and the helmet are coupled to each other, the wearing portion of the goggles is configured to secure the goggles, the face shield, and the helmet on the head of the worker.

8. The welder protector of claim 1, wherein:
the goggles are wearable independently of the face shield and the helmet.

9. The welder protector of claim 2, wherein:
when the goggles and the face shield are coupled to each other, the goggles protrusion and the face shield protrusion at least partially cover a gap between the first surface part of the goggles and the bent surface part of the face shield to prevent an intrusion of light, fumes, or spatter generated during welding.

10. A welder protector for protecting a worker, comprising:
a face shield including a first opening and a shield surface part surrounding the first opening, the face shield having a front shield surface and a rear shield surface, the front shield surface being configured to face away from the worker when being worn by the worker;
goggles detachably coupleable with the rear shield surface of the face shield and including a window portion, a frame that is configured to couple with the face shield, an extension member positioned inward of the frame, and a wearing portion, the window portion corresponding to the eyes of the worker, the wearing portion configured to extend at least partially around a head of the worker to secure the goggles on the head of the worker, wherein a goggles protrusion extends laterally outward from a laterally outward facing surface of the goggles; and
a helmet detachably coupleable with the face shield and including a second opening corresponding to the face shield, wherein:
the shield surface part of the face shield comprises a main surface part covering a side portion of the goggles and a bent surface part bent toward the first opening from the main surface part to form an angle with the main surface part;
the shield surface part comprises a face shield protrusion that extends laterally inward from the main surface part;
the extension member comprises an end portion that is configured to contact the face of the worker and prevent external light from proceeding towards the eyes of the worker, the end portion extending in a rearward direction beyond a rear end of the frame;
the helmet comprises a front helmet surface and a rear helmet surface, the front helmet surface being configured to face away from the worker when being worn by the worker;
the front shield surface is coupled with the rear helmet surface when the helmet is coupled with the face shield;
when the goggles and the face shield are coupled to each other, distal ends of the goggles protrusion and the face shield protrusion extend beyond one another in generally opposite directions and the goggles protrusion is disposed between the bent surface part and the face shield protrusion so as to maintain engagement between the goggles and the face shield;
when the goggles and the face shield are coupled to each other, the wearing portion of the goggles is configured to secure both the goggles and the face shield on the head of the worker;
when the goggles, the face shield, and the helmet are coupled to each other, the window portion of the goggles is exposed through the second opening of the helmet; and
when the goggles, the face shield, and the helmet are coupled to each other, the wearing portion of the goggles is configured to secure the goggles, the face shield, and the helmet on the head of the worker.

11. The welder protector of claim 10, wherein:
the goggles are configured to nest within a concave portion of the rear shield surface when the goggles and the face shield are coupled to each other.

12. The welder protector of claim 11, wherein:
the goggles and the face shield are configured to nest within a concave portion of the rear helmet surface when the goggles, the face shield, and the helmet are coupled to each other.

13. The welder protector of claim 10, wherein:
the wearing portion comprises an elastic band.

14. The welder protector of claim 10, wherein:
the goggles are wearable independently of the face shield and helmet.

15. The welder protector of claim 10, wherein:
the extension member defines an open volume extending between an end of the extension member and the window portion.

16. The welder protector of claim 15, wherein:
the extension member comprises an inclined surface that extends outward from a central axis of the extension member.

17. The welder protector of claim 10, wherein:
the goggles comprise a transparent substrate and an electronic optical element that is disposed inside the transparent substrate and comprises liquid crystal.

18. The welder protector of claim 10, wherein:
the face shield further comprises a light-emitting portion coupled with the shield surface part.

19. The welder protector of claim 18, wherein:
the light-emitting portion is disposed above the first opening.

* * * * *